United States Patent [19]

Sluetz

[11] Patent Number: 4,722,353

[45] Date of Patent: Feb. 2, 1988

[54] STABILIZER FOR IMPLANTABLE ELECTRODE

[75] Inventor: James E. Sluetz, Attleboro, Mass.

[73] Assignee: Intermedics, Inc., Freeport, Tex.

[21] Appl. No.: 776,255

[22] Filed: Sep. 16, 1985

[51] Int. Cl.⁴ ............................................... A61N 1/04
[52] U.S. Cl. ................... 128/785; 128/419 P; 128/783; 128/784; 128/786
[58] Field of Search ............... 128/419 P, 783, 784, 128/785, 786

[56] References Cited

U.S. PATENT DOCUMENTS

| | | | |
|---|---|---|---|
| 3,902,501 | 9/1975 | Citron et al. | 128/418 |
| 4,144,891 | 3/1979 | Lysfjord et al. | 128/419 P |
| 4,236,529 | 12/1980 | Little | 128/785 |
| 4,269,198 | 5/1981 | Stokes | 128/785 |
| 4,414,986 | 11/1983 | Dickhudt et al. | 128/785 |
| 4,432,377 | 2/1984 | Dickhudt | 128/786 |
| 4,506,679 | 3/1985 | Mann | 128/786 |
| 4,585,013 | 4/1986 | Harris | 128/785 |

FOREIGN PATENT DOCUMENTS 7909050 12/1979 Netherlands .................... 128/785

Primary Examiner—William E. Kamm
Assistant Examiner—Timothy Keegan
Attorney, Agent, or Firm—Fitch, Even, Tabin & Flannery

[57] ABSTRACT

A passive stabilizer for an electrode lead of a cardiac pacemaker for maintaining the electrode tip in interstitial contact with the endocardium until a sufficient amount of tissue ingrowth has occurred to secure the electrode tip in place. The passive stabilizer is secured to the lead of the cardiac stimulating device adjacent the electrode tip and comprises a sleeve having at least two groups of resilient tines, each group of tines being longitudinally displaced along the axis of the conductive lead with a first group being disposed between the second group and the electrode tip. The tines extend radially outwardly from the lead at a substantially right angle, with the tines of the first group extending outwardly a distance less than that of tines of the second group. Additionally, the tines of the first group are circumferentially staggered with respect to the tines of the second group.

6 Claims, 4 Drawing Figures

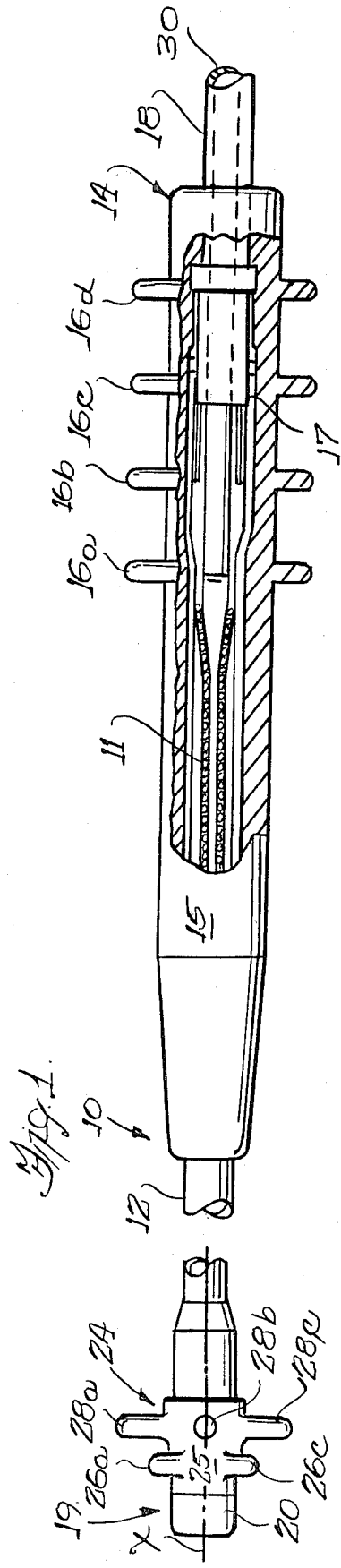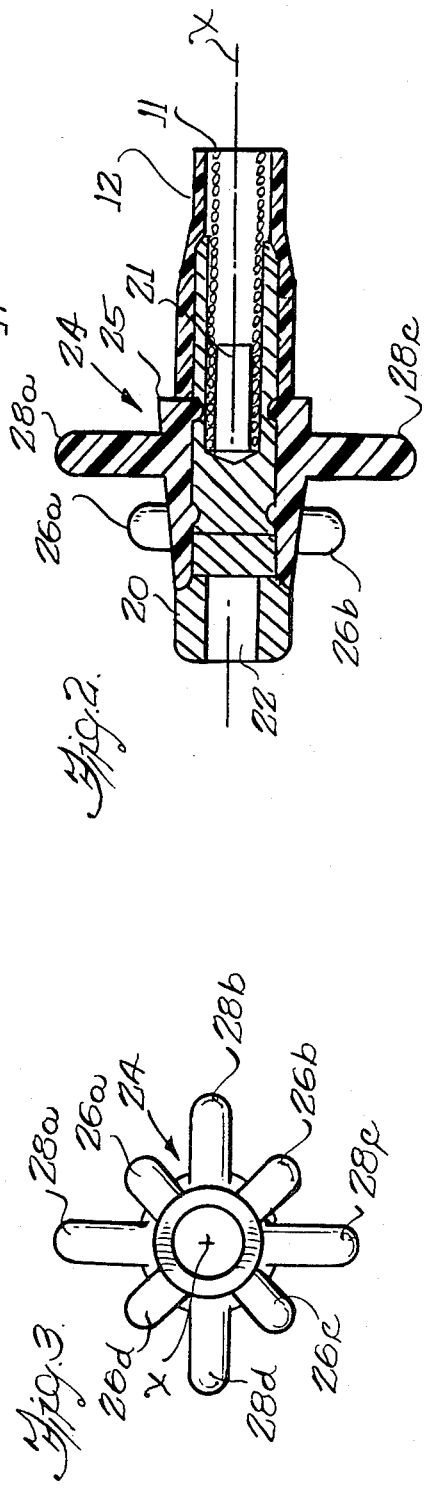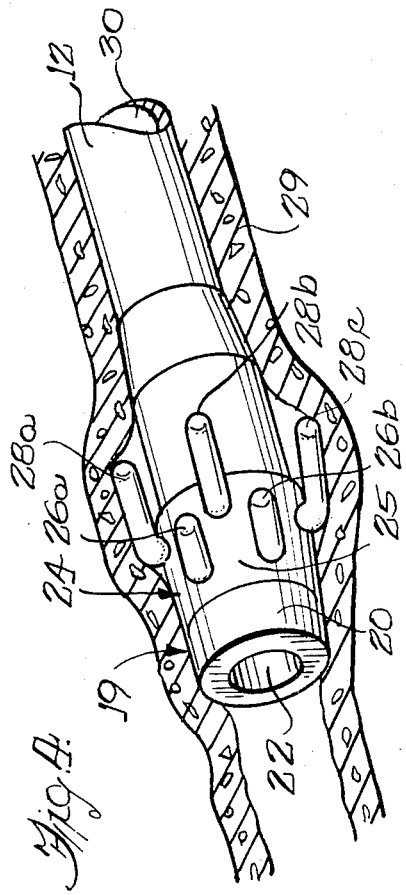

STABILIZER FOR IMPLANTABLE ELECTRODE

The present invention relates generally to an electrode lead used for electrical stimulation of the heart and, more particularly, to a dynamic stabilizer for such an electrode lead that passively maintains the electrode tip in interstitial contact with the endocardium until a sufficient amount of fibrosis of the heart tissue has occurred to secure the electrode tip in place.

BACKGROUND OF THE INVENTION

Electric cardiac pacemakers have proven effective in the long-term treatment of a large variety of heart dysfunctions, and accordingly, such devices constitute a preferred method of treating many of these afflictions. In general, pacemakers employ an electrode that is maintained in contact with the heart muscle, through which electrical stimulation of the heart muscle is achieved. Pacemakers commonly employ a flexible conductive lead that connects a remotely positioned power pack (usually implanted in a subcutaneous pocket beneath the pectoralis major or within the abdomen) to the electrode tip. The lead is typically routed through a vein leading to the heart so that the electrode is in contact with the heart muscle.

A particular problem associated with the implantation of such devices is the likelihood of dislodgement of the electrode tip from the heart wall occurring shortly after the implantation of the pacemaker. In an attempt to address this problem, active fixation means such as corkscrews or staples have been used to maintain the electrode tip in contact with the heart muscle. Alternatively, and preferably, passive fixation means have been employed to temporarily hold the electrode tip in contact with the heart muscle until sufficient tissue ingrowth has occurred about the electrode tip to hold it in place. Such a passive device is disclosed in Citron et al. U.S. Pat. No. 3,902,501, who provide a plurality of pliant tines extending from the electrode adjacent the tip and forming an acute angle with respect to the electrode body. The tines cooperate with the trabeculae in the heart muscle to hold the electrode tip in position until such time as natural fixation has occurred. However, because tines of the device of Citron et al. are angled acutely with respect to the electrode body, undue force is required to retract the lead once the tip has entered the heart chamber, as the tines must be folded back against the acute angle.

Accordingly, it is a principal object of the instant invention to provide a simplified passive fixation device for an electrode tip which does not hinder removal of the electrode from the heart chamber should that prove necessary.

It is a related object of the instant invention to provide a passive fixation device that assists in guiding the conductive lead of the pacemaker into a vein during implantation of the device.

These objects, and others which will become apparent upon reference to the accompanying drawings and following detailed description, are attained by a passive stabilizer that is secured to the lead of the cardiac stimulating device adjacent the electrode tip. The passive stabilizer comprises a sleeve having at least two groups of resilient tines, each group of tines being longitudinally displaced along the axis of the conductive lead with a first group being disposed between the second group and the electrode tip. The tines extend radially outwardly from the lead at a substantially right angle, with the tines of the first group extending outwardly a distance less than that of tines of the second group. Additionally, the tines of the first group are circumferentially staggered with respect to the tines of the second group.

Upon insertion of the conductive lead into a vein during the implantation of the pacemaker, the resilient tines fold back against the lead due to the constricting force of the vein. Because the tines of the two groups are circumferentially staggered, when the tines are forced to lay against the electrode lead during insertion, the tines of the one group will not interfere with the tines of the other group. After exiting from the vein into the desired heart chamber, the tines spring back to their original configuration in which the tines will interengage with the fibers in the heart muscle adjacent its wall to hold the electrode tip in place. In a preferred embodiment, there are four tines in each group, the tines in each group being circumferentially disposed from the adjacent tines in its group by approximately 90°. The tines of one group are, in turn, circumferentially staggered at an interval of approximately 45° with respect to the tines of the other group.

BRIEF DESCRIPTION OF THE DRAWINGS

FIG. 1 is an elevational view in partial cross-section showing a lead for a cardiac pacemaker including a passive fixation device adjacent the electrode tip incorporating the present invention.

FIG. 2 is a cross-sectional view of the distal end of the lead showing the electrode tip and passive fixation device.

FIG. 3 is a front elevational view of the passive fixation device showing the circumferential displacement of the tines in each of the two groups of tines.

FIG. 4 is a perspective view showing the distal end of the lead being inserted through a vein in which the tines are constricted so as to lay flat against the lead.

DETAILED DESCRIPTION OF THE PREFERRED EMBODIMENT

Turning to the figures of the drawings, there is seen in FIG. 1 a conductive lead, generally indicated by 10, to be used in conjunction with a remote power pack and pulse generating circuit (not shown) for implantation in a living body to provide bioelectric stimulation to, e.g., the heart. The lead 10 may be any of the state-of-the-art leads currently available. With respect to the illustrated lead 10, it is typically on the order of approximately 25 inches in length and includes a flexible conductive coil 11, preferably made of a nickel-cobalt alloy. The conductive coil 11 is contained within a tubing 12 made of a biocompatible medical-grade silicone rubber or polyurethane. The proximal end 14 of the lead 10 includes a connector sleeve 15 for receiving the power pack having integral sealing rings 16a–d and a connector pin 18 attached to the coil by means of a crimped sleeve 17 and a medical grade adhesive. The pin 18 connects the lead 10 to the power pack/pulse generating circuit of the pacemaker.

The distal end 19 of the lead 10, best seen in cross-section in FIG. 2, includes a ring tip electrode 20, preferably made of platinum or carbon-coated porous titanium and having either a flat or hemispherical end surface to promote electrical contact between the lead 10 and the heart wall. The end of the coil 11 receives a reinforcing slug 21, and the end of the coil 11, in turn, is received within the tip 20. The tip 20 is crimped about the slug 21 to secure the tip to the coil 11. In the illustrated tip 20, a plug 21 formed of a medical-grade silicone rubber adhesive fills the aperture in the end of the ring tip 20.

The distal end 19 of the conductive lead 10 is provided with means 24 for passively maintaining and stabilizing the tip 20 of the lead 10 in contact with the endocardium until such time as natural fixation due to ingrowth of tissue about the tip 20 has occurred. (The movement of the endocardium to which the electrode tip 20 is attached provides the "dynamic" aspect of the stabilizer.) In keeping with the invention, the stabilizing means 24 comprises a sleeve 25 having at least two groups 26, 28 of resilient tines. In practice, the tines are molded integrally with the sleeve of a biocompatible, medical-grade silicone rubber. The stabilizer 24 can be molded separately and then assembled with the lead, or it can be molded directly onto the lead. In the illustrated embodiment, there are four tines 26a–d and 28a–d in each group (best seen in FIG. 3). The two groups of tines 26, 28 are displaced with respect to each other along the longitudinal axis X of the lead 10, with the first group of tines 26 being disposed between the second group 28 and the electrode tip. The groups of tines 26, 28 are placed sufficiently close to the tip so as to engage the trabeculae or fibers in the endocardium to hold the electrode tip 20 in place. However, a sufficient area at the tip of the electrode must remain exposed in order to have an effective electrical contact between the lead 10 and the heart muscle. In practice, the first group of tines 26 is located approximately ⅛ inch from the end of the electrode tip 20, while the second group is disposed approximately 3/16 inch from the end of the tip 20.

Each tine in a group 26, 28 is equidistantly spaced about the circumference of the sleeve 25 from the adjacent tines in its group. Accordingly, with four tines in each group 26, 28, the tines 26a–d and 28a–d are spaced at substantially 90° intervals about the circumference of the sleeve 25 (best seen in FIG. 3). Additionally, the tines of the first group 26 are circumferentially staggered with respect to the tines of the second group 28, that is, the tines 26a–d are circumferentially displaced about the longitudinal axis X of the conductive lead 10 with respect to the tines 28a–d. Accordingly, in the illustrated embodiment, the tines of the first group 26 bisect the angles formed between the tines of the second group 28. Referring to FIG. 3, an angle of approximately 45° is formed between the tines 26a–d and 28a–d.

In order to ensure that both groups of tines 26, 28 are able to entangle with or interstitially engage the fibers of the endocardium, the tines of the first group 26 are of a lesser radial length of the tines of the second group 28. This provides a tapered appearance for the distal end 19 of the lead 10 and permits the inner tines 26a–d to extend into the narrowed regions between the muscle fibers while the outer tines 28a–d are still able to engage the outermost muscle fibers. In practice, each tine 26a–d extends radially from the longitudinal axis X a distance of approximately 3/32 inch, while each tine 28a–d has a radial length of approximately ⅛ inch.

Briefly describing a typical procedure in which a conductive lead 10 of the type described may advantageously be utilized, initially a vein leading to the heart is selected through which the lead 10 will be inserted. After the site is selected, the free end of the vein is tied off and the lead 10 is inserted into the portion leading to the heart. The tapered shape of the distal end 19 of the lead 10 assists in the initial insertion of the lead 10 into the selected vein 29 (FIG. 4). In order to ensure that the lead 10 is sufficiently rigid so that it may be forced through a confining vein, a stylet (not shown) is received within a lumen 30 through the connector pin 18 at the proximal end 14 of the lead 10. As the lead 10 passes through the vein 29, the resilient tines 26a–d and 28a–d are folded back by the constricting force of the vein as shown in FIG. 4 so as to substantially lie flat against the major surface of the sleeve 25 and the lead 10. Typically, the inside diameter of the vein is sufficiently confining so that all the tines 26a–d, 28a–d will be at least somewhat deflected. Because the tines of the first group 26a–d are circumferentially staggered with respect to the tines of the second group 28a–d, they are able to attain the position shown in FIG. 4 without any interference between the tines of the two groups.

The deflection of the tines 26a–d, 28a–d during insertion requires that the tines be sufficiently pliable so as to attain the folded-back configuration of FIG. 4 without exerting a force large enough to damage the vein wall. To ensure that this requirement is met, in practice the tines 26a–d, 28a–d have a circular cross-section with a diameter of approximately 0.030 inches and a hardness of approximately 50 Shore A. After the distal end 19 of the lead 10 enters an atrial or ventricular cavity, the tines 26a–d and 28a–d will spring back to their relaxed positions shown in FIGS. 1–3. The electrode tip 20 is then located against the wall of the cavity, proper placement of the electrode being checked through, e.g., a fluoroscope. When urged against the wall of the cavity, the tines 26a–d and 28a–d will interstitially engage the trabeculae to maintain the electrode tip 20 in place until such time as sufficient tissue ingrowth has occurred about the electrode tip to permanently hold the lead 10 in place. Once properly located, the stylet is withdrawn from the lead 10. Should it be required to remove the lead after the electrode tip has entered the heart chamber, the tines 26a–d an 28a–d simply fold back against the sleeve 25 in the reverse direction of that shown in FIG. 4. Because the tines 26a–d and 28a–d are substantially perpendicular to the sleeve, the retraction of the lead requires no more force than the insertion.

Accordingly, it can be seen that a dynamic stabilizing device for passively maintaining an electrode tip in interstitial contact with the heart muscle has been provided. While the invention has been described in terms of a preferred embodiment, such description is not intended to limit the invention to the same. On the contrary, it is intended to cover all equivalents falling within the scope of the appended claims. For example, while the stabilizing device has been described as having two groups of tines, additional groups may be utilized. Additionally, the number of tines within each group may be varied so long as the tines of the groups do not interfere with each other during the transvenous insertion of the lead.

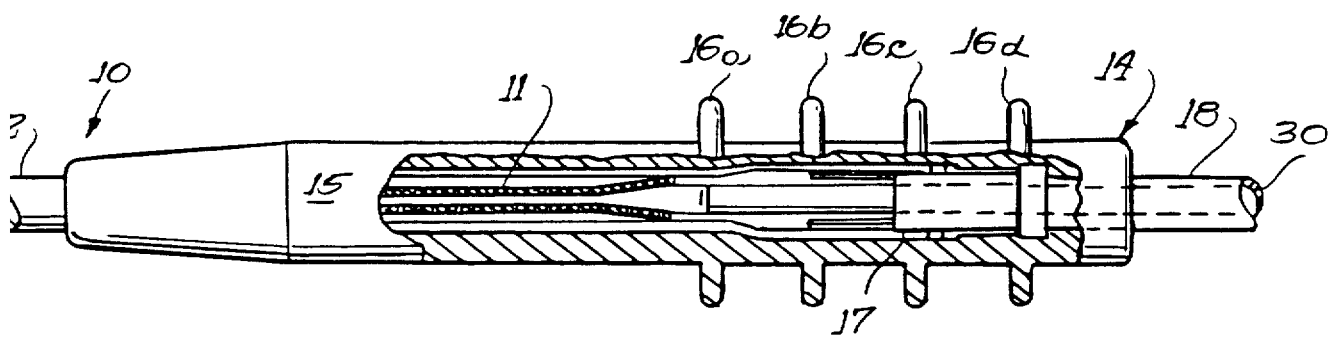

What is claimed is:

1. In a stimulator device including a lead with an electrode tip for transvenous implantation in a living body to provide electrical cardiac stimulation, stabilizing means secured to the lead adjacent the electrode tip for maintaining the electrode tip in electrical contact with the cardiac tissue, the stabilizing means comprising sleeve means having a major surface and at least two groups of resilient tines, each group of tines being longitudinally displaced along the axis of the lead with the first group being disposed between the second group and the electrode tip, the tines of each group extending radially outwardly from (a) the major surface of said sleeve means at (substantially) approximately a right angle thereto with the tines of the first group having radial length less thatn the tines of the second group, the tines of each group being circumferentially staggered with respect to the tines of the other group.

2. The combination of claim 1 wherein the number of tines in each group is four, the tines in each group being circumferentially displaced from the adjacent tines in its group by approximately 90°, and the tines of one group being circumferentially staggered at an interval of approximately 45° with respect to the tines of the other group.

3. The combination of claim 1 wherein the tines in the first group each have a radial length of approximately 3/32 inch and each of the tines in the second group have a radial length of approximately ⅛ inch.

4. The combination of claim 2 wherein the tines in the first group each have a radial length of approximately 3/32 inch and each of the tines in the second group have a radial length of approximately ⅛ inch.

5. The combination of claim 3 wherein the tines are made of silicone rubber and each tine has a thickness of approximately 0.030 inches, the second group of tines being disposed approximately 3/16 inch from the tip of the electrode, while the first group of tines is disposed approximately ⅛ inch from the tip of the electrode.

6. The combination of claim 4 wherein the tines are made of silicone rubber and each tine has a thickness of approximately 0.030 inches, the second group of tines being disposed approximately 3/16 inch from the tip of the electrode, while the first group of tines is disposed approximately ⅛ inch from the tip of the electrode, the flexibility of said silicone rubber being such that said tines fold back against said major surface of said sleeve means when said lead is inserted into a confining vein.

* * * * *

UNITED STATES PATENT AND TRADEMARK OFFICE
CERTIFICATE OF CORRECTION

PATENT NO. : 4,722,353

DATED : February 2, 1988

INVENTOR(S) : James E. Sluetz

It is certified that error appears in the above-identified patent and that said Letters Patent is hereby corrected as shown below:

The Title Page should be deleted to appear as per attached Title Page.

Column 5, line 5, after "having", insert --a--.

Column 5, line 6, corect the spelling of --than--.

Signed and Sealed this

Sixteenth Day of May, 1989

Attest:

DONALD J. QUIGG

Attesting Officer

Commissioner of Patents and Trademarks

United States Patent [19]
Sluetz

[11] Patent Number: 4,722,353
[45] Date of Patent: Feb. 2, 1988

[54] STABILIZER FOR IMPLANTABLE ELECTRODE

[75] Inventor: James E. Sluetz, Attleboro, Mass.

[73] Assignee: Intermedics, Inc., Freeport, Tex.

[21] Appl. No.: 776,255

[22] Filed: Sep. 16, 1985

[51] Int. Cl.⁴ ............................................. A61N 1/04
[52] U.S. Cl. ........................... 128/785; 128/419 P; 128/783; 128/784; 128/786
[58] Field of Search ............... 128/419 P, 783, 784, 128/785, 786

[56] References Cited

U.S. PATENT DOCUMENTS

| | | | |
|---|---|---|---|
| 3,902,501 | 9/1975 | Citron et al. | 128/418 |
| 4,144,891 | 3/1979 | Lysfjord et al. | 128/419 P |
| 4,236,529 | 12/1980 | Little | 128/785 |
| 4,269,198 | 5/1981 | Stokes | 128/785 |
| 4,414,986 | 11/1983 | Dickhudt et al. | 128/785 |
| 4,432,377 | 2/1984 | Dickhudt | 128/786 |
| 4,506,679 | 3/1985 | Mann | 128/786 |
| 4,585,013 | 4/1986 | Harris | 128/785 |

FOREIGN PATENT DOCUMENTS 7909050 12/1979 Netherlands .................. 128/785

Primary Examiner—William E. Kamm
Assistant Examiner—Timothy Keegan
Attorney, Agent, or Firm—Fitch, Even, Tabin & Flannery

[57] ABSTRACT

A passive stabilizer for an electrode lead of a cardiac pacemaker for maintaining the electrode tip in interstitial contact with the endocardium until a sufficient amount of tissue ingrowth has occurred to secure the electrode tip in place. The passive stabilizer is secured to the lead of the cardiac stimulating device adjacent the electrode tip and comprises a sleeve having at least two groups of resilient tines, each group of tines being longitudinally displaced along the axis of the conductive lead with a first group being disposed between the second group and the electrode tip. The tines extend radially outwardly from the lead at a substantially right angle, with the tines of the first group extending outwardly a distance less than that of tines of the second group. Additionally, the tines of the first group are circumferentially staggered with respect to the tines of the second group.

6 Claims, 4 Drawing Figures